(12) United States Patent
Nishikawa et al.

(10) Patent No.: US 10,376,426 B2
(45) Date of Patent: Aug. 13, 2019

(54) LOW-BULK, CLOSELY-FITTING DISPOSABLE ABSORBENT PANT FOR CHILDREN

(71) Applicant: The Procter & Gamble Company, Cincinnati, OH (US)

(72) Inventors: Masaharu Nishikawa, Cincinnati, OH (US); Urmish Popatlal Dalal, Milford, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 441 days.

(21) Appl. No.: 15/197,961

(22) Filed: Jun. 30, 2016

(65) Prior Publication Data

US 2017/0020746 A1   Jan. 26, 2017

Related U.S. Application Data

(60) Provisional application No. 62/186,551, filed on Jun. 30, 2015.

(51) Int. Cl.
*A61F 13/49* (2006.01)
*B32B 7/02* (2019.01)
(Continued)

(52) U.S. Cl.
CPC ...... *A61F 13/49011* (2013.01); *A61F 13/496* (2013.01); *A61F 13/49012* (2013.01); *B32B 5/022* (2013.01); *B32B 5/024* (2013.01); *B32B 5/08* (2013.01); *B32B 5/18* (2013.01); *B32B 7/02* (2013.01); *B32B 7/05* (2019.01); *B32B 7/14* (2013.01); *B32B 27/065* (2013.01); *B32B 27/12* (2013.01); *B32B 27/32* (2013.01); *A61F 2013/49055* (2013.01); *A61F 2013/49092* (2013.01); *B32B 2255/02* (2013.01); *B32B 2262/0253* (2013.01);
(Continued)

(58) Field of Classification Search
None
See application file for complete search history.

(56) References Cited

U.S. PATENT DOCUMENTS 3,860,003 A   1/1975   Buell
3,929,135 A   12/1975  Thompson
(Continued)

FOREIGN PATENT DOCUMENTS

EP   1 256 594 A1   11/2002
WO   WO 95/16746 A1   6/1995

OTHER PUBLICATIONS

PCT International Search Report dated Nov. 2, 2016, 2016 (12 pages).
(Continued)

*Primary Examiner* — Tatyana Zalukaeva
*Assistant Examiner* — Gabriella E Burnette
(74) *Attorney, Agent, or Firm* — William E. Gallagher

(57) ABSTRACT

A low-bulk disposable absorbent pant for a child is disclosed. The pant may have a belt structure formed of a stretch laminate of a pre-strained elastic film between two nonwoven layers. The belt may have a relaxed lateral size and a stretched lateral size that is at least 150% of the relaxed lateral size, the relaxed lateral size being no more than 400 mm. The pant may include one or more of waistband, leg band and supplemental elastic members.

13 Claims, 8 Drawing Sheets

(51) Int. Cl.
*B32B 7/14* (2006.01)
*B32B 27/32* (2006.01)
*A61F 13/496* (2006.01)
*B32B 7/05* (2019.01)
*B32B 27/12* (2006.01)
*B32B 5/08* (2006.01)
*B32B 5/02* (2006.01)
*B32B 5/18* (2006.01)
*B32B 27/06* (2006.01)

(52) U.S. Cl.
CPC ............. *B32B 2262/0261* (2013.01); *B32B 2262/0276* (2013.01); *B32B 2262/062* (2013.01); *B32B 2262/12* (2013.01); *B32B 2262/14* (2013.01); *B32B 2264/02* (2013.01); *B32B 2307/51* (2013.01); *B32B 2307/514* (2013.01); *B32B 2307/726* (2013.01); *B32B 2307/7265* (2013.01); *B32B 2555/02* (2013.01)

(56) References Cited

U.S. PATENT DOCUMENTS

| | | |
|---|---|---|
| 4,151,240 A | 4/1979 | Lucas |
| 4,324,246 A | 4/1982 | Mullane |
| 4,342,314 A | 8/1982 | Radel |
| 4,463,045 A | 7/1984 | Ahr |
| 4,472,328 A | 9/1984 | Sugimoto et al. |
| 4,552,709 A | 11/1985 | Thurman |
| 4,591,523 A | 5/1986 | Thompson |
| 4,610,678 A | 9/1986 | Weisman |
| 4,673,402 A | 6/1987 | Weisman |
| 4,777,073 A | 10/1988 | Sheth |
| 4,834,735 A | 5/1989 | Alemany |
| 4,834,741 A | 5/1989 | Sabee |
| 4,888,231 A | 12/1989 | Angstadt |
| 4,892,536 A | 1/1990 | DesMarais |
| 4,990,147 A | 2/1991 | Freeland |
| 5,037,416 A | 8/1991 | Allen |
| 5,137,537 A | 8/1992 | Herron |
| 5,147,345 A | 9/1992 | Young |
| 5,151,092 A | 9/1992 | Buell |
| 5,221,274 A | 6/1993 | Buell |
| 5,260,345 A | 11/1993 | DesMarais |
| 5,265,222 A | 11/1993 | Nishiya |
| 5,266,392 A | 11/1993 | Land |
| 5,342,338 A | 8/1994 | roe |
| 5,387,207 A | 2/1995 | Dyer |
| 5,397,316 A | 3/1995 | LaVon |
| 5,554,143 A | 9/1996 | Roe |
| 5,554,145 A | 9/1996 | Roe |
| 5,569,234 A | 10/1996 | Buell |
| 5,569,775 A | 10/1996 | Diaz et al. |
| 5,571,096 A | 11/1996 | Dobrin |
| 5,580,411 A | 12/1996 | Nease |
| 5,607,760 A | 3/1997 | Roe |
| 5,609,587 A | 3/1997 | Roe |
| 5,635,191 A | 6/1997 | Roe |
| 5,643,588 A | 7/1997 | Roe |
| 5,650,214 A | 7/1997 | Anderson et al. |
| 5,685,874 A | 11/1997 | Buell et al. |
| 5,733,628 A | 3/1998 | Pelkie |
| 5,865,823 A | 2/1999 | Curro |
| 5,916,661 A | 6/1999 | Benson |
| 6,004,306 A | 12/1999 | Robles |
| 6,107,537 A | 8/2000 | Elder |
| 6,169,151 B1 | 1/2001 | Waymouth |
| 6,383,431 B1 | 5/2002 | Dobrin et al. |
| 6,410,129 B2 | 6/2002 | Zhang |
| 6,518,378 B2 | 2/2003 | Waymouth |
| 6,555,643 B1 | 4/2003 | Rieger |
| 6,559,262 B1 | 5/2003 | Waymouth |
| 6,645,569 B2 | 9/2003 | James |
| 6,632,385 B2 | 10/2003 | Kauschke |
| 6,794,024 B1 | 9/2004 | Walton |
| 6,863,933 B2 | 3/2005 | Cramer |
| 7,112,621 B2 | 9/2006 | Rohrbaugh |
| 7,307,031 B2 | 12/2007 | Carroll |
| 7,507,587 B2 | 3/2009 | Chiba et al. |
| 8,105,303 B2 | 1/2012 | Sakaguchi |
| 8,177,766 B2 | 5/2012 | Mansfield |
| 8,186,296 B2 | 5/2012 | Brown et al. |
| 8,445,744 B2 | 5/2013 | Autran et al. |
| 8,529,725 B2 | 9/2013 | Bishop |
| 8,728,051 B2 | 5/2014 | Lu et al. |
| 8,852,482 B2 | 10/2014 | Curro et al. |
| 8,993,099 B2 | 3/2015 | Lightcap et al. |
| 9,216,116 B2 | 12/2015 | Roe et al. |
| 9,216,118 B2 | 12/2015 | Roe et al. |
| 9,326,899 B2 | 5/2016 | Zink et al. |
| 9,532,908 B2 | 1/2017 | Wade et al. |
| 2003/0023219 A1* | 1/2003 | Nakaoka ............... A61F 13/496 604/385.01 |
| 2003/0148684 A1 | 8/2003 | Cramer |
| 2004/0133181 A1* | 7/2004 | Ishiguro ............ A61F 13/49001 604/385.28 |
| 2004/0192140 A1 | 9/2004 | Schneider et al. |
| 2005/0008839 A1 | 1/2005 | Cramer et al. |
| 2006/0057921 A1 | 3/2006 | Turi |
| 2006/0173436 A1* | 8/2006 | Krautkramer ...... A61F 13/49011 604/393 |
| 2007/0073256 A1 | 3/2007 | Ponomarenko |
| 2008/0287897 A1* | 11/2008 | Guzman Reyes .......................... A61F 13/15699 604/365 |
| 2011/0092943 A1* | 4/2011 | Bishop .............. A61F 13/15577 604/385.29 |
| 2012/0071852 A1 | 3/2012 | Tsang |
| 2012/0316528 A1 | 12/2012 | Kruezer et al. |
| 2014/0134910 A1 | 5/2014 | Mansfield |
| 2014/0343522 A1 | 11/2014 | Arai et al. |
| 2015/0080837 A1 | 3/2015 | Rosati et al. |
| 2015/0088088 A1 | 3/2015 | Wade et al. |
| 2015/0173957 A1* | 6/2015 | Schneider ........... A61F 13/1565 493/374 |
| 2015/0182388 A1 | 7/2015 | Katsuragawa |
| 2016/0022510 A1* | 1/2016 | Hashimoto ........... A61F 13/496 604/385.26 |
| 2017/0000660 A1 | 1/2017 | Wade et al. |

OTHER PUBLICATIONS

All Office Actions for U.S. Appl. No. 15/197,961.
All Office Actions for U.S. Appl. No. 14/755,090.

* cited by examiner

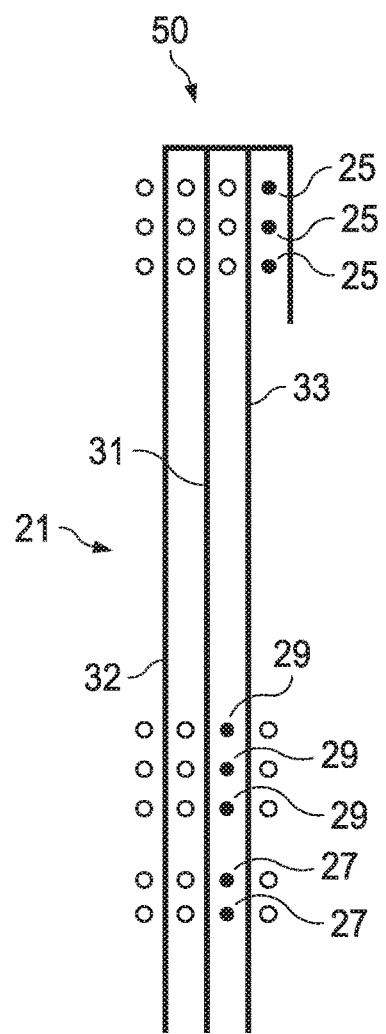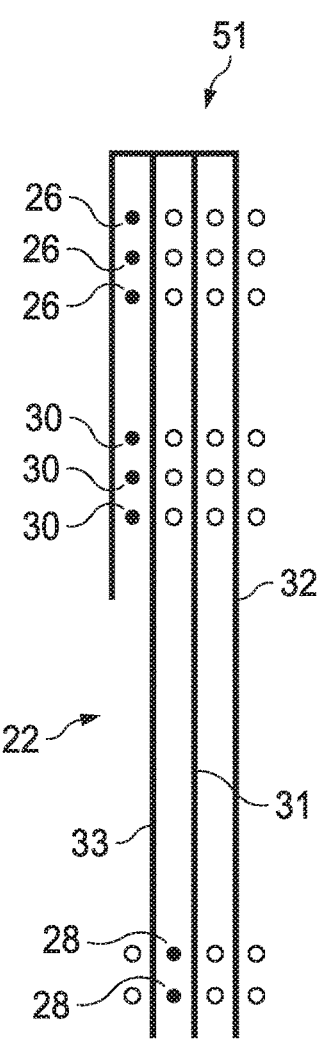
FIG. 3A
FIG. 3B

LOW-BULK, CLOSELY-FITTING DISPOSABLE ABSORBENT PANT FOR CHILDREN

CROSS REFERENCE TO RELATED APPLICATION

This application claims the benefit of U.S. Provisional Application No. 62/186,551, filed Jun. 30, 2015, the substance of which is incorporated herein by reference.

BACKGROUND OF THE INVENTION

Currently, disposable absorbent pants are manufactured and marketed for wear by toddlers and young children who are not yet toilet trained or who are experiencing childhood enuresis. A disposable absorbent pant usually includes a central absorbent chassis having a core formed of absorbent material, enveloped between a liquid permeable, wearing-facing topsheet, and a liquid impermeable, outer- or garment-facing backsheet. The chassis is usually adapted to be positioned on the wearer such that it wraps between the wearer's legs and upwardly about the lower torso, such that the front and rear ends extend toward the wearer's waistline in the front and rear, respectively. The chassis is usually joined to a pair of side/hip panels that each connects front and rear regions of the chassis on either side thereof, thereby forming a pant structure. In many current designs, the side/hip panels are manufactured so as to be elastically extensible in the lateral direction, providing stretchability that facilitates donning, while providing a relatively snug and comfortable fit once donned. Disposable absorbent pants are usually manufactured in one of two differing overall configurations.

In the first configuration, the backsheet and topsheet of the central chassis structure extend to, and form, the front and rear waist edges of the pant in the regions near the wearer's navel in the front, and small of the back in the rear. Separate and discrete side/hip panels are joined at their proximal portions to longitudinal (side) edges of the central chassis structure in its front and rear regions, and joined together at their respective distal portions to form the pant structure. An example of this type of configuration is currently manufactured and sold in the United States by The Procter & Gamble Company under the trademark PAMPERS EASY UPS.

In the second configuration, components of the central chassis structure do not extend to, or form, the front and rear waist edges of the pant. Rather, an elasticized belt structure entirely encircles the wearer's waist and forms the waist edge about the entire pant, and forms the side/hip panels. The central chassis is joined to the belt structure, usually on the inside thereof, with its ends disposed at locations in the front and rear waist regions somewhat below the waist edges of the belt structure. This second configuration is sometimes known as a "belt" or "balloon" configuration (hereinafter, "belt" configuration). Examples of this type of configuration are currently manufactured and sold in Asia by The Procter & Gamble Company under the trademark PAMPERS, and by Unicharm Corporation under the trademark MAMY POKO.

While both configurations have their advantages, in some circumstances a belt configuration may be deemed desirable. Among other advantages, because the encircling belt may be made elastically extensible in the lateral direction, considerable elastic stretch and contraction may be provided entirely about the wearer's waist. The belt configuration also lends itself to certain manufacturing and product design efficiencies, and it is believed to be gaining in consumer preference.

In current belt configuration products for child wearers, the belt structure typically is formed of a plurality of laterally-oriented, longitudinally-spaced elastic strands, sandwiched between two layers of nonwoven web to form a stretch laminate. During manufacturing the elastic strands are typically incorporated into the structure in a pre-strained (elongated) condition. When the completed belt structure is allowed to relax (as upon completion of manufacture of the pant), the elastic strands contract toward their unstrained lengths and draw the nonwoven web layers along with them, causing the nonwoven web layers to form ruffles or gathers of material along the lateral length of the belt structure. These ruffles or gathers impart what some consumers may deem a ruffled or frilly appearance to the belt portion of the pant. Some consumers may find this aesthetically attractive, and some consumers may perceive that the ruffles or gathers impart softness and breathability to the belt structure, contributing to wearer comfort. On the other hand, the ruffles and gathers occupy volume and contribute to what may be perceived as a bulky appearance and feel. The appearance also may be perceived as a signal that the pant is a "diaper," which some consumers may perceive negatively for various reasons. For example, older children who are toilet training or experiencing childhood enuresis may prefer a pant that looks more like a pair of underwear.

Thus, opportunities exist for improvements and/or variants in the design and construction of disposable absorbent pants of a belt configuration, which have appeal for consumers of varying preferences.

DESCRIPTION OF THE DRAWINGS

FIG. 3A is a longitudinal cross-section view of the front belt portion of the pant structure of FIG. 2;

FIG. 3B is a longitudinal cross-section view of the rear belt portion of the pant structure of FIG. 2;

DESCRIPTION OF EXAMPLES

Definitions

Figure 1:
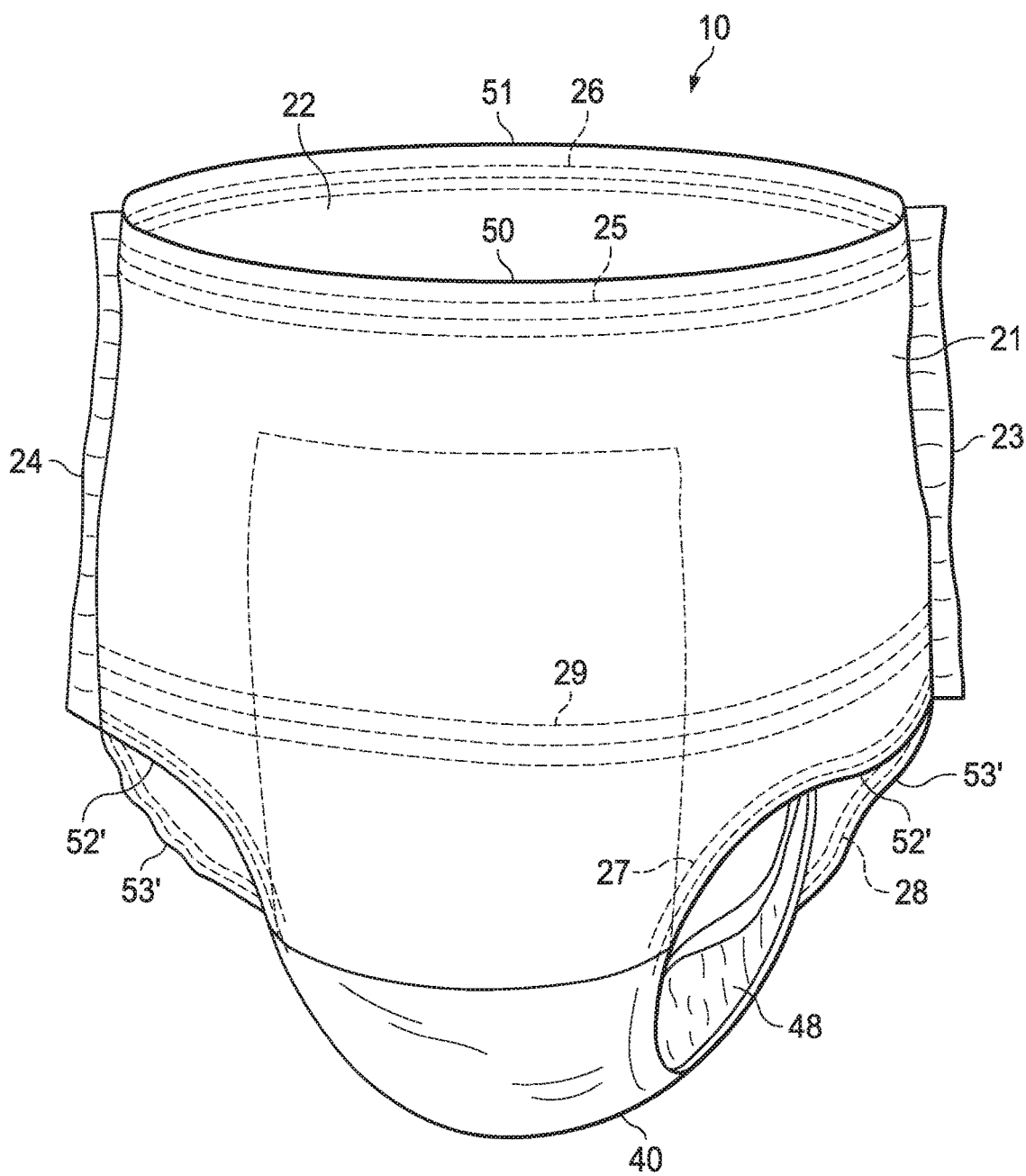
FIG. 1 is a perspective view of an absorbent pant.

"Cross direction" (CD)—with respect to the making of a nonwoven web material, the nonwoven material itself, or a laminate thereof, refers to the direction along the material substantially perpendicular to the direction of forward travel of the material through the manufacturing line in which the material and/or article is manufactured.

As used herein, the term "elastic" or "elastomeric" refers to the property of an extensible material (or a composite of multiple materials) that can extend, without substantial rupture or breakage, to a strain of 100% in the Hysteresis Test, with a set less than or equal to 30% of the elongation as measured according to the Hysteresis Test. An elastic material is considered elastically extensible.

"Film" means a non-fibrous skin- or membrane-like material formed in part or in whole of one or more polymer resins.

"Machine direction" (MD)—with respect to the making of a nonwoven web material, the nonwoven material itself, or a laminate thereof, refers to the direction along the material substantially parallel to the direction of forward travel of the material through the manufacturing line in which the material and/or article is manufactured.

"Lateral"—with respect to a pant and its wearer, refers to the direction generally perpendicular with the wearer's standing height, or the horizontal direction when the wearer is standing. With respect to a disposable absorbent article that is opened (not connected at side seams) and laid out flat on a horizontal surface, "lateral" is also the direction generally perpendicular to a line extending from the midpoint of the front waist edge to the midpoint of the rear waist edge.

"Longitudinal"—with respect to a pant and its wearer, refers to the direction generally parallel with the wearer's standing height, or the vertical direction when the wearer is standing. With respect to a disposable absorbent article that is opened (not connected at side seams) and laid out flat on a horizontal surface, "longitudinal" is also the direction generally parallel to a line extending from the midpoint of the front waist edge to the midpoint of the rear waist edge.

"Nonwoven," or interchangeably, "nonwoven web" means a fibrous cloth-like material formed of discrete staple fibers, or long or substantially continuous fibers or filaments, or any combination thereof that are neither knitted nor woven, but rather, are distributed along a plane in at least somewhat random orientation, accumulated, consolidated and held together to form a cohesive web structure by one or more of friction, entanglement, adhesive bonding, through-air (melt) bonding, thermal bonding or other bonding. Nonwovens may be formed by processes including, for example, spunbonding, meltblowing, airlaying, coforming and carding, hydroentangling and/or other processes used to manufacture such materials.

A "strip" of material is an elongate section of material having a length, width and thickness; the length is the longest dimension; the width and thickness are measured along a plane orthogonal to the longest dimension; the thickness is the shortest dimension; and the ratio of the width to the thickness (aspect ratio of cross section orthogonal to length) is at least 2. A "strand" of material is an elongate section of material with its length being its longest dimension, and having a cross section orthogonal to its length having an aspect ratio less than 2.

Referring now to FIGS. 1 and 2, disposable absorbent pant 10 may be formed of an absorbent chassis 40 having a front end 16 affixed via any suitable mechanism to a front belt portion 21 and a rear end 17 affixed to a rear belt portion 22. During manufacture, the precursor structure may be folded about lateral axis 100 with inner surfaces of the front and rear portions facing each other, and respective longitudinal side edges of the front and rear belt portions 21, 22 may be joined at left and right side seams 23, 24 to form the completed pant 10 structure as shown in FIG. 1. The side seams 23, 24 may be permanent or refastenable. Permanent seams may be formed of mechanical, thermal and/or adhesive bonds between the materials respectively forming front belt portion 21 and rear belt portion 22. Refastenable seams may be formed by any mechanism that provides for substantially non-destructive separation of front belt portion 21 and rear belt portion 22 at the seams, and reattachment thereof, including but not limited to adhesive tape and cooperating components; hook and loop fastening systems, etc. The precursor structure and the completed pant 10 have a front waist region 101 including the front belt portion 21, a rear waist region 102 including the rear belt portion 22, and a crotch region 103 that bridges the front waist region and the rear waist region across lateral axis 100. When the pant is worn, the crotch region 103 is disposed between the wearer's legs.

Belt Structure

Figure 2A:
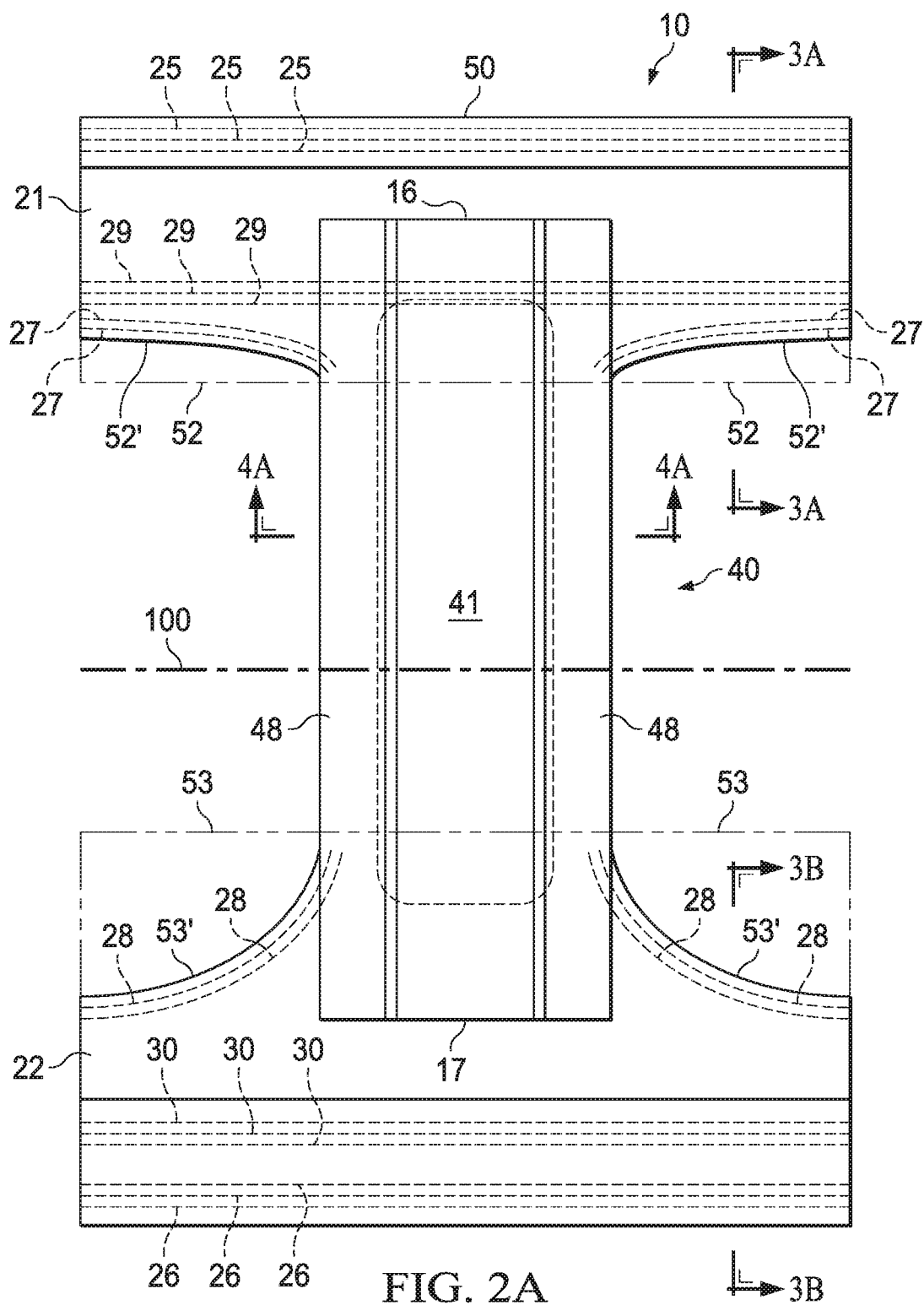
FIG. 2A is a plan view of an absorbent pant structure shown not connected at side seams and laid out flat on a horizontal surface, stretched out against contraction induced by pre-strained elastic members, with wearer-facing surfaces facing the viewer.

Referring to FIGS. 2A, 3A and 3B, one or both of front and rear belt portions 21, 22 may be formed of a laminate of an elastic film member 31 sandwiched between first and second nonwoven layers 32, 33. The front and rear belt portions 21, 22 may be rectangular in shape, with substantially straight lower front and/or rear leg edges 52, 53, or alternatively, may have portions cut out therefrom, for curved, more tailored front and/or rear leg edges 52', 53'. The elastic film member 31 may extend the entire area of either or both of the front and rear belt portions, or alternatively, may be foreshortened in either or both the longitudinal and lateral directions of one or both of the front and rear belt portions such that it is not present in, e.g., portions of the areas within the seams 23, 24; portions proximate the crotch region and/or overlying the absorbent chassis 40 (to the garment-facing side thereof); and/or portions proximate the waist edges 50, 51. In some examples, elastic film may be omitted (e.g., cut out) in at least part of the areas of the belt portion(s) overlying the chassis. This may be desired because the chassis may not be deemed suitable for lateral elastic stretch and contraction; such lateral contraction could create a bunched and/or bulky appearance and/or be uncomfortable for the wearer. Accordingly, inclusion of elastic film over the chassis may be deemed unnecessary consumption of elastomeric material from which the film is made. In other examples, it may be deemed more efficient for manufacturing or other purposes to leave the portion of the elastic film member overlying and extending across the chassis in place within the belt laminate. In order to avoid lateral contraction of the chassis with lateral contraction of the part of the belt portion overlying the chassis, the elastic film member 31 may be deactivated by, e.g., application of heat that relieves pre-strain in the elastic film member 31, in area(s) overlying the chassis.

Figure 2B:
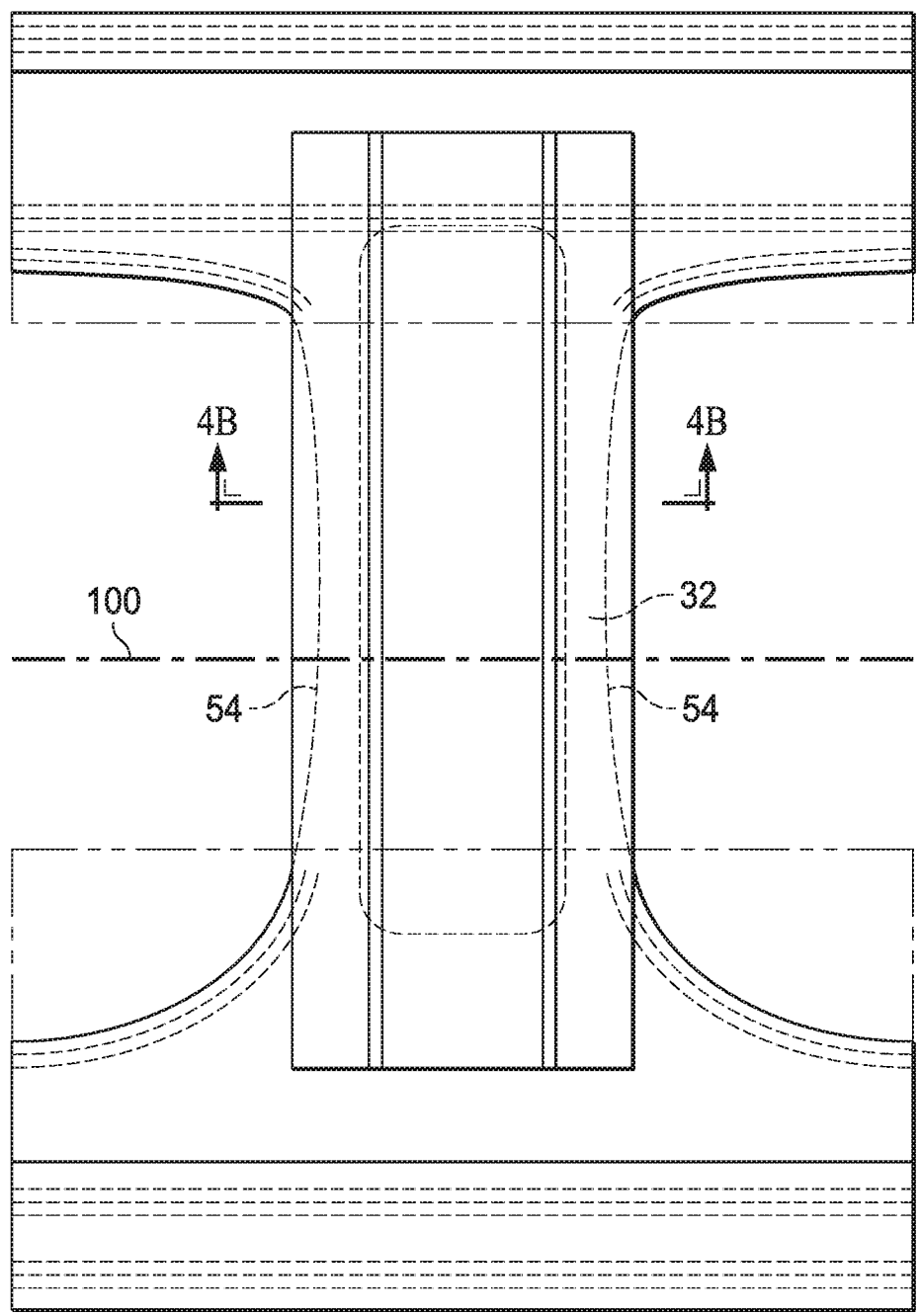
FIG. 2B is a plan view of an alternative example of an absorbent pant structure shown not connected at side seams and laid out flat on a horizontal surface, stretched out against contraction induced by pre-strained elastic members, with wearer-facing surfaces facing the viewer.
Figure 4A:
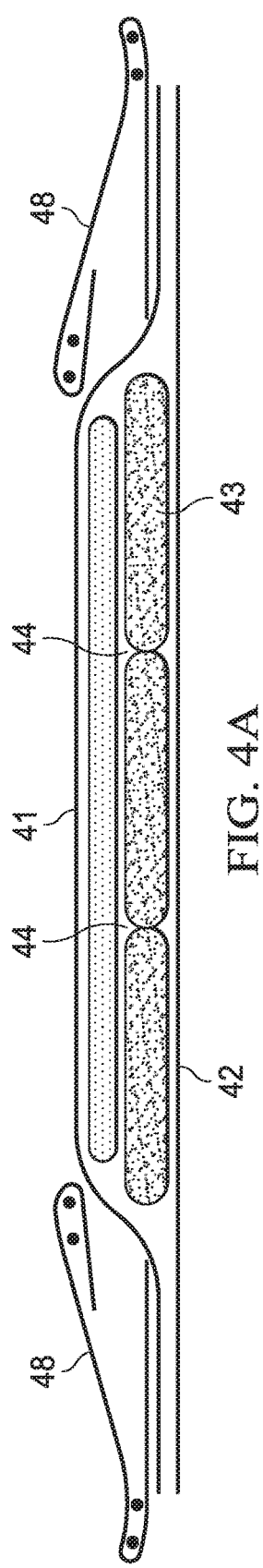
FIG. 4A is a lateral cross-section view taken through line 4-4 the chassis of the pant structure of FIG. 2.
Figure 4B:
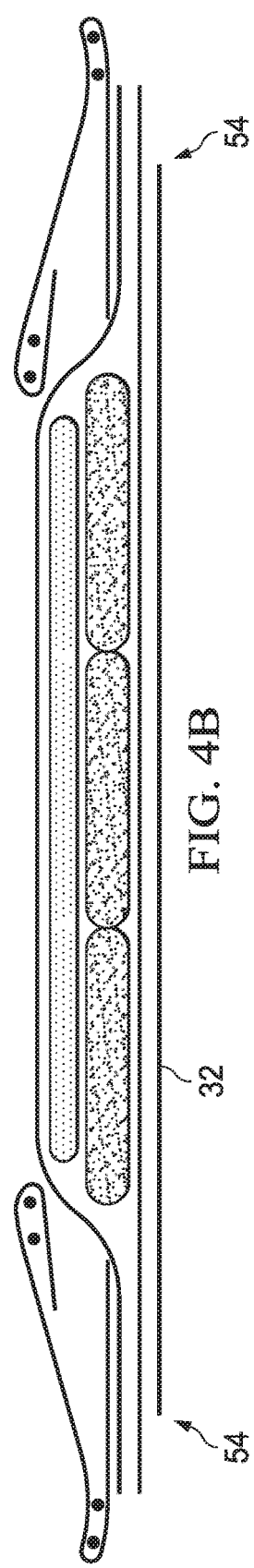
FIG. 4B is a lateral cross-section view taken through line 4-4 the chassis of the pant structure of FIG. 2B.
Figure 5:
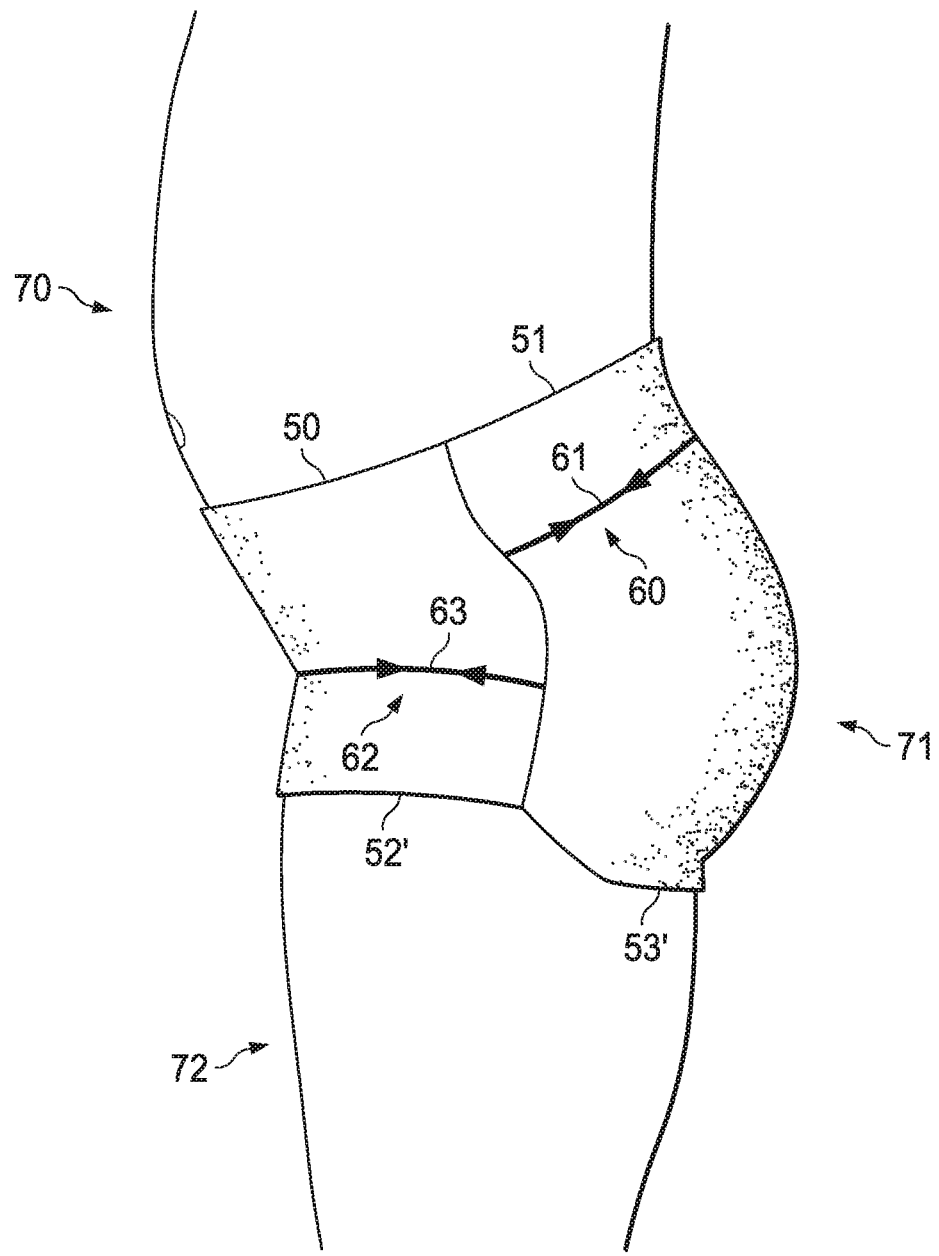
FIG. 5 is a simplified schematic side view of a pant structure shown on the lower torso of a standing wearer.

Referring to FIGS. 2B and 4B, in an alternative example, the pant may have a unibody construction. In such an example, front and rear belt portions 21, 22 may share at least one, single, continuous nonwoven layer 32 and/or 33 that extends from the front belt portion 21 through the crotch region to the rear belt portion 22, forming a layer of each. In a more particular example, the shared nonwoven layer includes at least the outermost (garment-facing) layer of each of the belt portions. When such outermost layer is continuous over the outside of both belt portions and through the crotch region, this helps impart the pant with a unitized, particularly garment-like appearance. The continuous layer(s) may be cut along each of the leg openings in concave profiles 54 in the crotch region as suggested in FIG. 2B, to create or enhance a tailored appearance.

Elastic film member 31 may be formed of any suitable elastomeric film. Examples of elastomeric film and/or compositions from which suitable elastomeric film may be formed are described in, for example, U.S. Pat. Nos. 8,177, 766 and 6,794,024; and U.S. Pat. Pub. No. 2014/0134910.

Additional suitable elastomeric compositions comprise thermoplastic elastomers selected from the group consisting of styrenic block copolymers, metallocene-catalyzed polyolefins, polyesters, polyurethanes, polyether amides, and combinations thereof. Suitable styrenic block copolymers may be diblock, triblock, tetrablock, or other multi-block copolymers having at least one styrenic block. Exemplary styrenic block copolymers include styrene-butadiene-styrene, styrene-isoprene-styrene, styrene-ethylene/butylenes-styrene, styrene-ethylene/propylene-styrene, and the like. Commercially available styrenic block copolymers include KRATON from Kraton Performance Polymers, Inc. of Houston, Tex.; SEPTON from Kuraray America, Inc. of New York, N.Y.; and VECTOR from TSRC Dexco Chemical Company of Houston, Tex.

Semi-crystalline, or metallocene, polyolefins are widely used in disposable absorbent products. It is known that their performance depends on amount of crystallinity. The crystallinity decreases with decreasing stereoregularity, and the material shows more elastic behavior. A number of methods are known for controlling crystallinity, such as by introducing stereo-irregularity or by introducing a co-monomer. The polyolefin elastomer materials useful herein include, but are not limited to, any polymers or copolymers of polyolefins such as polyethylene and polypropylene. Particularly suitable examples of elastic materials include elastomeric polypropylenes. In these materials, propylene represents the majority component of the polymeric backbone, and as a result, any residual crystallinity possesses the characteristics of polypropylene crystals. Residual crystalline entities embedded in the propylene-based elastomeric molecular network may function as physical crosslinks, providing polymeric chain anchoring capabilities that improve the mechanical properties of the elastic network, such as high recovery, low set and low force relaxation. Suitable examples of elastomeric polypropylenes include an elastic random poly(propylene/olefin) copolymer, an isotactic polypropylene containing stereo-irregularity, an isotactic/atactic polypropylene block copolymer, an isotactic polypropylene/random poly(propylene/olefin) copolymer block copolymer, a stereoblock elastomeric polypropylene, a syndiotactic polypropylene block poly(ethylene-co-propylene) block syndiotactic polypropylene triblock copolymer, an isotactic polypropylene block regioirregular polypropylene block isotactic polypropylene triblock copolymer, a polyethylene random (ethylene/olefin) copolymer block copolymer, a reactor blend polypropylene, a very low density polypropylene (or, equivalently, ultra-low density polypropylene), a metallocene polypropylene, and blends or combinations thereof. Suitable polypropylene polymers including crystalline isotactic blocks and amorphous atactic blocks are described, for example, in U.S. Pat. Nos. 6,559,262; 6,518, 378; and 6,169,151. Suitable isotactic polypropylene with stereo-irregularity along the polymer chain are described in U.S. Pat. No. 6,555,643 and EP 1 256 594 A1. Suitable examples include elastomeric random copolymers including propylene with a low level comonomer (e.g., ethylene or a higher alpha-olefin) incorporated into the backbone.

Such polyolefin elastomer materials may be selected from commercially available materials such as, but not limited to: Vistamaxx 6102 (available from ExxonMobil, Houston, Tex.), random propylene-ethylene copolymers; NOTIO PN-0040 and PN-2070 (available from Mitsui Chemicals, Tokyo Japan), elastic polyolefin resins; L-MODU X901 S (available from Mitsui Chemicals, Tokyo Japan): a stereo copolymer of polypropylene; Versify 2400A, 2400B, 3401A and 3401B (available from Dow Chemical, Midland, Mich.), random copolymers of propylene with ethylene; INFUSE (available from DOW Chemical, Midland, Mich.), block copolymer of ethylene with alpha olefin.

Commercially available polyurethanes include ESTANE from Lubrizol, Inc., Ohio, polyether amides include PEBAX from Arkema Chemicals of Philadelphia, Pa., and polyesters include HYTREL from E. I. DuPont de Nemours Co., of Wilmington, Del. can be suitable elastomer for the product making.

The elastomer composition of the elastic film may include one or more additives commonly used in the art to tailor the composition for a particular use. For example, stabilizers, antioxidants, and bacteriostats may be employed to prevent thermal, oxidative, and bio-chemical degradation of the elastomer composition. Generally, the additive or additives may account for 0.01% to 20%; 0.01% to 10%; or even 0.01% to 2% of the total weight of the elastomer composition.

Suitable examples of stabilizers and antioxidants include high molecular weight hindered phenols (i.e., phenolic compounds with sterically bulky radicals in proximity to the hydroxyl group), multifunctional phenols (i.e., phenolic compounds with sulfur and phosphorous containing groups), phosphates such as tris-(p-nonylphenyl)-phosphite, hindered amines, and combinations thereof. Representative hindered phenols include t-butylhydroxyquinone; 1,3,5-trimethyl-2, 4,6-tris(3-5-di-tert-butyl-4-hydroxybenzyl) benzene; pentaerythritol tetrakis-3(3,5-di-tert-butyl-4-hydroxyphenyl) propionate; n-octadecyl-3(3,5-ditert-butyl-4-hydroxyphenyl) propionate; 4,4'-methylenebis(4-methyl-6-tert butyl-phenol); 4,4'-thiobis(6-tert-butyl-o-cresol); 2,6-di-tert-butylphenol; 6-(4-hydroxyphenoxy)-2,4-bis(n-ocytlthio)-1,3, 5-triazine; 2,4,6-tris(4-hydroxy-3,5-di-tert-butyl-phenoxy)-1,3,5-triazine; di-n-octadecyl-3,5-di-tert-butyl-4-ydroxybenzylphosphonate; 2-(n-octylthio)ethyl-3,5-di-tert-butyl-4-hydroxybenzoate; and sorbitol hexa-(3,3,5-di-tert-butyl-4-hydroxy-phenyl) propionate. Proprietary commercial stabilizers and/or antioxidants are available under a number of trade names including a variety of Wingstay®, Tinuvin® and Irganox® products.

Examples of suitable bacteriostats include benzoates, phenols, aldehydes, halogen containing compounds, nitrogen compounds, and metal-containing compounds such as mercurials, zinc compounds and tin compounds. A representative bacteriostat is 2,4,4'-trichloro-2'-hydroxy-diphenyl-ether which is available under the trade designation IRGASAN PA from Ciba Specialty Chemical Corporation, Tarrytown, N.Y.

Various viscosity modifiers, processing aids, slip agents or anti-block agents can be employed as additives to provide improved handling characteristics or surface characteristics. Processing aids include processing oils, which are well known in the art and include synthetic and natural oils, naphthenic oils, paraffinic oils, olefin oligomers and low molecular weight polymers, vegetable oils, animal oils, and derivatives of such including hydrogenated versions. Processing oils also may incorporate combinations of such oils. A particularly suitable processing oil is mineral oil.

A variety of fillers can also be used as additives to the elastomer composition. Examples of suitable fillers include talc, calcium carbonate, carbon black, clay, and mica. The filler may be selected in combination with antioxidants to minimize impact on stability. A wide range of pigments can also be employed to impart desirable color to the elastomer composition. Organic and inorganic pigments such as azo, quinacridone, cadmium, and chrome containing pigments may be blended with the elastomer composition.

Nucleating agents such as sorbitol based compounds, sodium salts of organic phosphates, sodium benzoate may be used in combination with the elastomer composition. They help improve optical properties and physical properties of the elastomer composition. Compatiblizers can also be used in combination with the elastomer composition. They help improve interfacial adhesion between components. This often results in better mechanical and/or optical properties.

Film—Breathability; Pore Forming; Aperturing

When a material used to form a layer component of a wearable article allows water vapor to pass therethrough (vapor permeable), it may be described as "breathable." Breathability may help keep the wearer's skin dry and comfortable. Nonwovens of the type contemplated herein for use to make nonwoven layers 32, 33 are typically inherently highly breathable as a feature of their open fibrous structure. Elastomeric films, however, may generally be inherently less breathable.

Films have been traditionally used to provide liquid barrier properties in limited use or disposable absorbent articles such as disposable diapers and disposable absorbent pants, and in, for example backsheet components thereof. Elastomeric films have been used as stretch mechanisms in other components, such as elastically extensible diaper fastening members and hip/side panels. Although films may be effective barriers with respect to containing liquid exudates, they might not be optimal for comfort and skin health because they may be insufficiently vapor permeable (i.e., insufficiently breathable) so as to allow water vapor to pass through and escape the article and thereby avoid discomfort and overhydration of the wearer's skin beneath the material that includes the film.

There are a number of known ways of making a film breathable, including aperturing and the use of fillers. Breathable polyolefin films can be produced by stretching a precursor film filled with a filler such as calcium carbonate particles. Breathable films which are gas/vapor permeable and liquid impermeable are taught by U.S. Pat. No. 4,472,328. The '328 patent teaches a breathable polyolefin film prepared from a polyolefin/filler composition having from 20 percent to 80 percent by weight of a filler such as a surface treated calcium carbonate. A liquid or waxy hydrocarbon polymer elastomer was reportedly found to produce a precursor film that could be monoaxially or biaxially stretched to make the film breathable. U.S. Pat. No. 4,777,073 teaches a breathable film produced from a precursor film that is prepared from a polymer composition comprising at least one polyolefin component and a filler. Suitable polyolefins for film production are indicated to include polypropylene, copolymers of propylene, homopolymers and copolymers of ethylene or blends thereof. Suitable fillers are indicated to be any organic or inorganic material having a low affinity for and a significantly lower elasticity than the polyolefin component, or no elasticity at all, preferably a rigid material having a non-smooth hydrophobic surface or a material which is treated to render its surface hydrophobic.

PCT International Patent Publication No. WO 99/14044 teaches a, breathable elastic laminate comprising a water vapor permeable, elastic film material loaded with a filler having a particle size suitable for pore formation and a nonwoven web bonded to the elastic film, the film being stretched in at least two directions. The stretching of the film renders the film microporous and, thus, breathable, or, in the case of films which are initially breathable, more breathable. The breathable elastomeric film is a metallocene-catalyzed polyethylene polymeric resin material comprising a filler material of at least 10% by volume of the film. The metallocene-catalyzed polyethylene polymeric resin material has a density of from 0.850 to 0.917 g/cc, and the film comprises from 10% by volume to 50% by volume filler. Although this material may have good elastic properties, a film having better elastic properties than metallocene-catalyzed polyethylene elastomers may be desired in some circumstances. One such film is disclosed by U.S. Pat. No. 5,733,628, which teaches breathable, elastic polymeric film laminates employing apertured films made from high performance elastomeric materials such as styrene block copolymers.

One problem which has been found when using filled elastomers for producing breathable stretch-thinned films is the tendency of the micropores formed during the stretch-thinning process to close up upon release of the stretching force due to the elastic recovery properties of the elastomers. This is particularly true of high performance elastomers like styrene block copolymers. As a result, there has always been a tradeoff between breathability and stretch and recovery properties for stretch-thinned filled elastic materials.

Accordingly, in some examples, it may be desirable to provide pre-formed apertures (i.e., apertures that are intentionally provided in the film during a manufacturing process) that extend through the thickness of the film. Alternatively, apertures may be formed through the film during or after the laminating process in which the laminate forming the belt portions is made. In one example, apertures may be formed through the entire laminate, i.e., through both nonwoven layers and the film sandwiched therebetween, simultaneously.

The apertures may have any suitable size and/or shape desired. For example, the apertured film may have circle-shaped, individual apertures with a diameter of between 0.2 and 3 mm and an open area of 5-60% (e.g., 10-30% or 15-25%). In another example, the apertured film may include slits that can "opened up" by applying a transverse force to form round, rectangular, diamond-shaped apertures, combinations of these, and/or any other suitable shape desired with a largest dimension in the x-y plane of the film of between 0.2 and 3 mm. In still another example, the apertures may extend three-dimensionally through the film and form a conelike structure. In such an example, the tapered, cone-like structure may include a first opening having a first diameter in the plane of the film (major diameter) and a second opening having a second, smaller diameter at the opposing end of the cone (minor diameter). Aperture size and open area may be measured according to the method set forth in U.S. Publication No. 2007/0073256. Suitable methods for forming apertures in a film may include, for example, die punching, slitting, hot-pin melt aperturing, vacuum forming, high pressure jet aperturing, embossing rolls, combinations of these and the like. In conventional films, aperture pattern selection may be largely dictated by the need to minimize stress concentration around the apertures, thereby mitigating the risk of tearing the film during mechanical activation. But the film disclosed herein is not so limited, and therefore may provide improved manufacturing flexibility when selecting an aperture pattern and/or size. Suitable examples of apertured films and methods of aperturing films are disclosed in U.S. Pat. Nos. 6,410,129; 7,307,031; 4,151,240; 4,552,709; 3,929,135; 4,324,246; 4,342,314; 4,463,045 and 4,591,523.

Nonwoven Layers

The nonwoven layers 32, 33 may be formed of any suitable nonwoven web material. Suitable nonwoven web materials that may be useful in the present invention also include, but are not limited to spunbond, spunlaid, meltblown, spunmelt, solvent-spun, electrospun, carded, film fibrillated, melt-film fibrillated, air-laid, dry-laid, wet-laid staple fibers, and other and other nonwoven web materials formed in part or in whole of polymer fibers, as known in the art. The nonwoven web may be formed predominately of polymeric fibers. In some examples, suitable non-woven fiber materials may include, but are not limited to polymeric materials such as polyolefins, polyesters, polyamide, or specifically, polypropylene (PP), polyethylene (PE), polylactic acid (PLA), polyethylene terephthalate (PET) and/or blends thereof. In some examples, the fibers may be formed of PP/PE blends such as described in U.S. Pat. No. 5,266,392. Nonwoven fibers may be formed of, or may include as additives or modifiers, components such as aliphatic polyesters, thermoplastic polysaccharides, or other biopolymers. Further useful nonwovens, fiber compositions, formations of fibers and nonwovens and related methods are described in U.S. Pat. Nos. 6,645,569; 6,863,933; and U.S. Pat. No. 7,112,621; and in co-pending U.S. patent applications Ser. Nos. 10/338,603; 10/338,610; and 13/005,237.

The individual fibers may be monocomponent or multicomponent. The multicomponent fibers may be bicomponent, such as in a core-and-sheath or side-by-side arrangement. Often, the individual components comprise polyolefins such as polypropylene or polyethylene, or their copolymers, polyesters, thermoplastic polysaccharides or other biopolymers.

According to one example, the nonwoven may comprise a material that provides good recovery when external pressure is applied and removed. Further, according to one example, the nonwoven may comprise a blend of different fibers selected, for example from the types of polymeric fibers described above. In some embodiments, at least a portion of the fibers may exhibit a spiral curl which has a helical shape. According to one example, the fibers may include bicomponent fibers, which are individual fibers each comprising different materials, usually a first and a second polymeric material. It is believed that the use of side-by-side bi-component fibers is beneficial for imparting a spiral curl to the fibers.

In order to enhance softness perceptions of the laminate, nonwovens may be treated by hydrojet impingement, which may also be known as hydroenhancement, hydroentanglement or hydroengorgement. Such nonwovens and processes are described in, for example, U.S. Pat. Nos. 6,632,385 and 6,803,103, and U.S. Pat. App. Pub. No. 2006/0057921.

Other examples of nonwoven web that may be useful in the present laminate may be an SMS web (spunbond-meltblown-spunbond web) made by Avgol Nonwovens LTD, Tel Aviv, Israel, under the designation XL-S70-26; a softband SSS (spunbond-spunbond-spunbond) web made by Pegas Nonwovens AS in Znojmo, Czech Republic, under the designation 18 XX 01 00 01 00 (where XX=the variable basis weight); an SSS web made by Gülsan Sentetik, Gaziantep, Turkey, under the designation SBXXF0YYY (where XX=the variable basis weight, and YYY=the variable cross direction width); an HESB (hydroenhanced spunbond) web made by First Quality Nonwovens Inc., in Hazelton, Pa., under the designation SEH2503XXX (where XXX=the variable cross direction width); and a bicomponent SS web.

A nonwoven web useful as a component to form one or both of layers 32, 33 may be pre-bonded. A batt of fibers may be calendered and pre-bonded in a pattern, to consolidate the batt/fibers and create a pattern of bonds that adds tensile strength and dimensional stability, converting the batt of fibers to a coherent and useable nonwoven web material. The web may be imparted with a pattern of pre-bonding as described in, for example, U.S. Pat. No. 5,916,661 (pre-bonding in a pattern of "point calendered bonds 200 to form a coherent web structure") and U.S. application Ser. No. 13/893,405 (pattern of "primary fiber bonds"). The pre-bonding may consist of a pattern of thermal bonds, mechanical bonds or adhesive bonds, although in some circumstances thermal bonding may be preferred.

During manufacture of the belt laminate, the elastomeric film material used to form elastic film member 31 may be incorporated into the laminate and affixed to the nonwoven layers 32, 33 in a pre-strained condition, while the nonwoven layers 32, 33 are not substantially strained. The direction of pre-strain may be the lateral direction with respect to the finished pant product. Upon relaxation of the laminate following manufacture, the elastic film member 32 will contract laterally toward its unstrained lateral dimension, and in doing so, will draw nonwoven layers 32, 33 along with it, causing nonwoven layers 32, 33 to form gathers with valleys and ridges transverse to the direction of pre-strain. Because film provides a much greater amount of surface area to which the nonwoven layers 32, 33 may be bonded or otherwise affixed as compared with longitudinally-spaced elastic strands (as in typical belt configuration disposable absorbent pants), the number of bonds or other points or areas of affixation between elastic member and nonwoven layers can be much greater. As a result, the gathers in the nonwoven layers may be made comparatively much smaller and more densely spaced than those in belts with strand elastics. The gathers may be made so small and dense as to be nearly unnoticeable to the naked eye, giving the belt structure a thin, cloth-like appearance, and substantially reduced bulkiness, as compared with a belt structure having strand elastics and a bulky appearance. As may be appreciated, the size, shape and pattern of the gathers formed may be affected by appropriate selection of a pattern for laminating adhesive or a pattern of thermal bonds, or a combination thereof, used to bond the layers of the laminate together.

To enhance an appearance of breathability of the layers 32 and/or 33, and to provide visual enhancement, the nonwovens of which either layer or both layers are formed may be apertured as disclosed in, for example, U.S. application Ser. No. 14/032,595. The nonwovens may be apertured and may also be incrementally stretched to cause the apertures to open or change shape, both processes occurring prior to lamination with elastic film member 31 to form the belt portions. As described in the above-cited '595 application, the apertures can be included to impart a lively, complex texture and appearance, and an appearance of enhanced breathability, to the laminate. Thus, it may be particularly preferred that the outer nonwoven layer of one or both belt portions be apertured since the outer layer will be visible on the outside of the pant.

Lateral Supplemental Elastic Members

In order to keep the gathers in nonwoven layers 32, 33 effectively small so as to maintain a non-bulky, cloth-like appearance, it may be desirable to limit the amount of lateral pre-strain imparted to the elastic film member 31 during incorporation into the belt structure. Thus, while it may be desirable that the stretched lateral size of the pant is at least 150% of the relaxed lateral size of the pant, it may also be desirable that the stretched lateral size be limited to a maximum of 300% of the relaxed lateral size. In other examples, the stretched lateral size of the pant may be from 175% to 300% of the relaxed lateral size, or even from 200% to 300%. While this may have the effect of helping limit the size and bulkiness of the gathers, it may also tend to limit the amount of elastic extensibility (stretch) the finished belt structure will have. It is believed that consumers prefer sufficient "room" within the belt structure to accommodate easy donning on and removal of the pant from the wearer. Thus, when the amount of lateral pre-strain of the elastic film member 31 is limited, elastic extensibility is limited and the belt may need to be made laterally wider (of greater circumference) to provide the desired room. With reduced extensibility, however, the larger belt may not laterally contract sufficiently to provide a consistently snug, secure and durable fit on the wearer (in other words, it may fit about the waist and hips too loosely).

In order to remedy this situation, elastic members in addition to elastic film member 31 may be added to the belt structure. Referring to FIGS. 2, 3A and 3B, front and/or rear waistband elastic members 25, 26 may be added to the structure proximate the front and rear waist edges 50, 51 of the belt structure. Similarly, front and/or rear leg band elastic members 27, 28 may be added to the structure proximate the front and rear leg opening edges 52, 53 of the structure. Such waistband and leg band elastic members may help further draw the belt material snug about the waist and/or leg openings, providing a neat, low-bulk underwear-like appearance and a snug fit that minimizes chances that exudates can escape the pant and soil outer clothing or surroundings.

Referring to FIGS. 2, 3A, 3B and 5, to further enhance likelihood of a secure and conforming fit, front and/or rear lateral supplemental elastic members may be added to the belt structure. These may be located so as to help the structure better conform to the wearer's anatomical features. Young children often exhibit exaggerated prominence in the belly 70, buttocks 71 and thigh 72 regions, as suggested in FIG. 5. Locating one or more rear lateral supplemental elastic members 30 at an upper location 60 in the rear, such that the members 30 may provide supplemental lateral contractive force 61 in the belt structure over the tops of the wearer's buttocks, which may tend to better anchor the pant on the wearer in a manner that resists downward pull by forces resulting from, e.g., weight of absorbed liquid contained in the absorbent core. Similarly, locating one or more front lateral supplemental elastic members 29 at a lower location 62 at or about the front juncture between the wearer's upper thighs and lower torso as suggested in FIG. 4, may provide supplemental lateral contractive force 63 in the belt structure over the tops of the wearer's thighs. This may both help resist downward pull and also help hold the article more closely to the wearer and thereby reduce an appearance of bulkiness in the front of the pant. Thus, when lateral supplemental elastic members are included in both front and rear, it may be desired that the rear lateral supplemental elastic member(s) 30 and the front lateral supplemental elastic member(s) 29 be longitudinally offset from each other, and even more preferably, that the rear lateral supplemental elastic member(s) be disposed longitudinally closer to the waist edge than the front lateral supplemental elastic member(s) 29, as suggested in the figures. For purposes herein, lateral supplemental elastic members respectively located in front and rear are "longitudinally offset" from each other when the collective center of mass for the front supplemental members and the collective center of mass for the rear supplemental members do not lie at the same longitudinal distance from a waist edge. For purposes herein, lateral supplemental elastic members are distinguished from waistband elastic members (e.g., members 25, 26) in that waistband elastic members are disposed 40 mm or less from the waist edge, while lateral supplemental elastic members are disposed more than 40 mm from the waist edge. For purposes herein, lateral supplemental elastic members are distinguished from leg band elastic members (e.g., members 27, 28) in that leg band elastic members are disposed 30 mm or less from the leg opening edge, while lateral supplemental elastic members are disposed more than 30 mm from the leg opening edge.

Any of front waistband elastic member(s) 25, rear waistband elastic member 26, front leg band elastic members 27, rear leg band elastic members 28, front lateral supplemental elastic member(s) 29 and rear lateral supplemental elastic members(s) 30 may comprise or be formed of strands or strips of elastomeric material, including but not limited to, the elastomeric materials described in more detail herein. Further, any combination of strands or strips of elastomeric material may be used to form any of these members individually, or in combination. For example, strips of elastomeric material may be used to form waistband elastomeric members and/or leg band elastomeric members, and strands of elastomeric material may be used to form lateral supplemental elastic members. In the non-limiting examples depicted in FIGS. 3A and 3B, strands of elastomeric material form all of waistband elastic members 25, 26, leg band elastic members 27, 28, and front and rear lateral supplemental elastic members 29, 30.

As suggested in FIGS. 3A and 3B, it may be desirable to locate the added elastic members within the structure so as to be sandwiched between inner and outer layers such as nonwoven layers, to at least partially conceal them, provide added structure in which to fix them in place longitudinally, and protect them from dislodgement. In the examples depicted, waist band elastic members 25, 26 are located to the outside of one of first and second nonwoven layers 32, 33, and then concealed, sandwiched and protected by an overwrapping portion of first nonwoven layer 32. In the examples depicted, leg band elastic members 27, 28 are sandwiched along with elastic film member 31 between first and second nonwoven layers 32, 33. Supplemental elastic members 29 are shown sandwiched between first and second nonwoven layers 32, 33 in the front, and supplemental members 30 between second nonwoven layer 33 and an overwrapping portion of first nonwoven layer 32 in the rear. As may be appreciated and as indicated in the figures, however, a variety of configurations are possible, although it may be desirable in any situation that added elastic members be sandwiched between inner and outer layers, for the reasons stated above.

If strands are used the added elastic members 25, 26, 27, 28, 29, 30 may be formed of any suitable strands formed of elastomeric material, such as an elastane (for example, LYCRA HYFIT fiber, a product of Invista, Wichita, Kans.). In other examples, the one or more elastic members may be strips or a section of film formed of elastomeric material.

The elastic members may also be formed from various other materials, such as but not limited to, rubbers, styrene ethylbutylene styrene, styrene ethylene propylene styrene, styrene ethylene ethylene propylene styrene, styrene butadiene styrene, styrene isoprene styrene, polyolefin elastomers, elastomeric polyurethanes, and other elastomeric materials known in the art, and combinations thereof. In some embodiments, the elastic members can be extruded strand elastics with any number of strands (or filaments). The elastic members can have a decitex ranging from 50 to 2000, or any integer value for any decitex value in this range, or any range formed by any of these integer values.

The elastomeric members may be in a form of strips of film. Examples of suitable films include, for example, those described, in U.S. Pat. App. Pub. No. 2010/0040826. The film may be created with a variety of resins combined in at least one of several sublayers, the latter providing different benefits to the film. Elastic strips for use as any of elastic members 25, 26, 27, 28, 29, 30 may also be cut from any of the elastic film materials described elsewhere herein and in the references cited.

Chassis Structure

Referring to FIGS. 2 and 4, absorbent chassis 40 may generally have any structure that is suitable for disposable absorbent articles such as diapers and training pants, including any of the absorbent core and leg cuff/gasketing structures described and depicted in U.S. application Ser. No. 13/457,521. The chassis 40 may include a liquid permeable topsheet 41, a backsheet 42, and an absorbent core 43 between the topsheet 41 and the backsheet 42. The absorbent core 43 may have a body-facing surface and a garment facing-surface. The topsheet 41 may be joined to the core 43 and/or the backsheet 42. The backsheet 42 may be joined to the core 43 and/or the topsheet 41. It should be recognized that other structures, elements, or substrates may be positioned between the core 43 and the topsheet 41 and/or backsheet 42. While the topsheet 41, the backsheet 42, and the absorbent core 43 may be assembled in a variety of configurations, examples are described generally in U.S. Pat. Nos. 3,860,003; 5,151,092; 5,221,274; 5,554,145; 5,569,234; 5,580,411; and 6,004,306.

The topsheet 41 is generally a portion of the chassis 40 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers (e.g., polyester, polyolefin e.g. polyethylene or polypropylene fibers), or a combination of natural and synthetic fibers. The topsheet 41 is generally supple, soft feeling, and non-irritating to a wearer's skin. Generally, at least a portion of the topsheet 41 is liquid pervious, permitting liquid to readily penetrate through its thickness. One topsheet 41 useful herein is available from BBA Fiberweb, Brentwood, Tenn. as supplier code 055SLPV09U.

Any portion of the topsheet 41 may be coated with a lotion or skin care composition. Examples of suitable lotions include those described in U.S. Pat. Nos. 5,607,760; 5,609,587; 5,635,191; and 5,643,588. The topsheet 41 may be fully or partially elasticized or may be foreshortened so as to provide a void space between the topsheet 41 and the core 43. Exemplary structures including elasticized or foreshortened topsheets are described in more detail in U.S. Pat. Nos. 4,892,536; 4,990,147; 5,037,416; and 5,269,775.

The absorbent core 43 may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. In one embodiment, at least a portion of the absorbent core is substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material does not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The amount of absorbent material, such as absorbent particulate polymer material present in the absorbent core may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. Non-limiting examples of suitable absorbent cores are described in greater detail below.

Exemplary absorbent structures for use as the absorbent core 43 are described in U.S. Pat. Nos. 4,610,678; 4,673,402; 4,834,735; 4,888,231; 5,137,537; 5,147,345; 5,342,338; 5,260,345; 5,387,207; 5,397,316; and 5,625,222.

The backsheet 42 is generally positioned such that it may be at least a portion of the garment-facing surface 120 of the pant. Backsheet 42 may be designed to prevent the exudates absorbed by and contained within the pant from soiling articles that may contact the absorbent article 20, such as bed sheets or outer clothing. In some examples, the backsheet 42 is effectively liquid-impermeable. Suitable backsheet 42 materials include films such as those manufactured by Tredegar Industries Inc. of Terre Haute, Ind. and sold under the trade names X15306, X10962, and X10964. Other suitable backsheet 42 materials may include breathable materials that permit vapors to escape from the pant while still preventing liquid exudates from passing through the backsheet 42. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE.

Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 42 including, but not limited to, surface treatments, particular film selections and processing, particular filament selections and processing, etc.

Backsheet 42 may also consist of more than one layer. The backsheet 42 may comprise an outer cover and an inner layer. The outer cover may be made of a soft, non-woven material. The inner layer may be made of a substantially liquid-impermeable film. The outer cover and an inner layer may be joined together by adhesive or any other suitable material or method. A particularly suitable outer cover is available from Corovin GmbH, Peine, Germany as supplier code A18AH0, and a particularly suitable inner layer is available from RKW Gronau GmbH, Gronau, Germany as supplier code PGBR4WPR. While a variety of backsheet configurations are contemplated herein, various other changes and modifications can be made without departing from the spirit and scope of the invention.

The absorbent core 43 and components thereof also may be constructed to provide a system of substantially longitudinally-oriented channels 44 as disclosed in, for example, U.S. applications Ser. Nos. 13/491,642; 13/491,644; 13/675,212; 13/709,169; 13/709,244; 13/709,254; and 14/077,355. As noted in the cited applications, a system of one or more substantially longitudinally-oriented channels in the absorbent core structure provides for efficient liquid distribution across the absorbent structure, and also a relatively thinner and more flexible core structure, contributing to an overall sleek, low-bulk, underwear-like look and feel to the pant structure. The channels 44 are grooves or valleys defined through the absorbent material of the core. They may perform at least two functions, including providing passageways along which liquid may rapidly flow to reach and contact surface area of more absorbent material along the length of the absorbent core, and providing hinge- or joint-like structures in the absorbent core structure along which the absorbent core may more easily flex, providing comfort and bulk-reducing effects.

Hysteresis Test

Obtain samples of subject material sufficient to provide for a gauge length of at least 15 mm along the direction of stretch in the Test, and should be of a constant width (perpendicular to the direction of stretch in the Test) of at least 5 mm.

The Hysteresis Test can be used to various specified strain values. The Hysteresis Test utilizes a commercial tensile tester (e.g., from Instron Engineering Corp. (Canton, Mass.), SINTECH-MTS Systems Corporation (Eden Prairie, Minn.) or equivalent) interfaced with a computer. The computer is used to control the test speed and other test parameters and for collecting, calculating, and reporting the data. The tests are performed under laboratory conditions of 23° C.±2° C. and relative humidity of 50%±2%. The samples are conditioned for 24 hours prior to testing.

Test Protocol

1. Select the appropriate grips and load cell. The grips must have flat surfaces and must be wide enough to grasp the sample along its full width. Also, the grips should provide adequate force to ensure that the sample does not slip during testing. The load cell is selected so that the tensile response from the sample tested is between 25% and 75% of the capacity of the load cell used.

2. Calibrate the tester according to the manufacturer's instructions.

3. Set the distance between the grips (gauge length) at 15 mm.

4. Place the sample in the flat surfaces of the grips such that the uniform width lies along a direction perpendicular to the gauge length direction. Secure the sample in the upper grips, let the sample hang slack, then close the lower grips. Set the slack preload at 0.02 N/cm. This means that the data collection starts when the slack is removed (at a constant crosshead speed of 10 mm/min) with a force of 0.02 N/cm. Strain is calculated based on the adjusted gauge length ($l_{ini}$), which is the length of the sample in between the grips of the tensile tester at a force of 0.02 N/cm. This adjusted gauge length is taken as the initial sample length, and it corresponds to a strain of 0%. Percent strain at any point in the test is defined as the change in length divided by the adjusted gauge length times 100.

5(a) First cycle loading: Pull the sample to the specified strain (herein, 100%) at a constant cross head speed of 100 mm/min. Report the stretched sample length between the grips as $l_{max}$.

5(b) First cycle unloading: Hold the sample at the specified strain for 30 seconds and then return the crosshead to its starting position (0% strain or initial sample length, $l_{ini}$) at a constant cross head speed of 100 mm/min. Hold the sample in the unstrained state for 1 minute.

5(c) Second cycle loading: Pull the sample to the specified strain at a constant cross head speed of 100 mm/min.

5(d) Second cycle unload: Next, return the crosshead to its starting position (i.e. 0% strain) at a constant cross head speed of 100 mm/min.

A computer data system records the force exerted on the sample during the test as a function of applied strain. From the resulting data generated, the following quantities are reported (note that loads are reported as force divided by the width of the sample and do not take into account the thickness of the sample):

i. Length of sample between the grips at a slack preload of 0.02 N/cm ($l_{ini}$) to the nearest 0.001 mm.

ii. Length of sample between the grips on first cycle at the specified strain ($l_{max}$) to the nearest 0.001 mm.

iii. Length of sample between the grips at a second cycle load force of 0.02 N/cm ($l_{ext}$) to the nearest 0.001 mm.

iv. % set, which is defined as $(l_{ext}-l_{ini})/(l_{max}-l_{ini})*100\%$ to the nearest 0.01%. The testing is repeated for six separate samples and the average and standard deviation reported.

The Hysteresis Test can be suitably modified depending on the expected attributes and/or properties of the particular material sample to be measured. For example, the Test can be suitably modified where a sample of the length and width specified above are not available from the subject pant.

Lateral Size Measurement

This method is used to measure the waist circumference of an absorbent pant at a relaxed state and a stretched state.

Figure 6A:
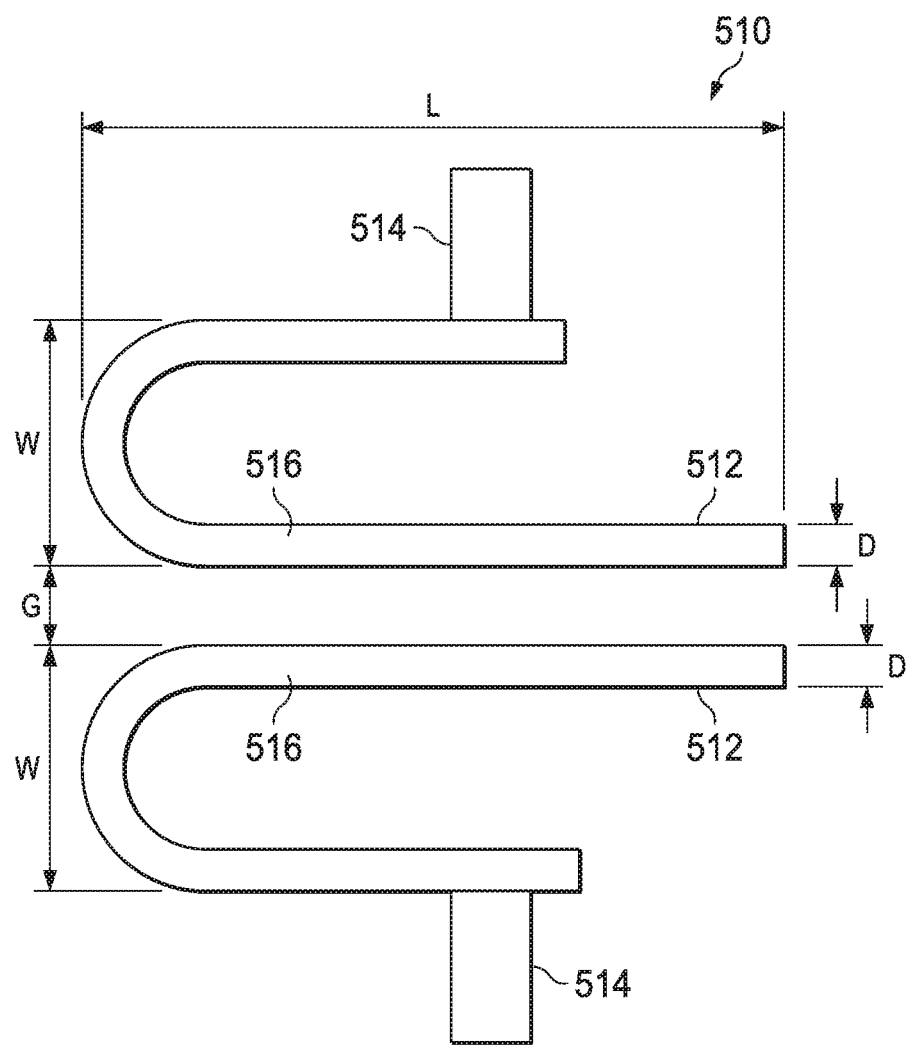
FIGS. 6A and 6B depict hook fixtures to be used in the Lateral Size Measurement method herein.

The lateral size measurement is performed on a tensile tester with a computer interface. An exemplary tester is an MTS Synergy tensile tester interfaced with Testworks 4 software. The test is conducted at ambient room conditions with a temperature of 23° C.±1° C. and a relative humidity of 50%±2%. For this test, the tensile tester is fitted with a 100N load cell and custom hook fixtures 510 as shown in FIG. 6A.

The hook fixtures 510 are a pair of J-shaped hooks 512 each with an attachment member 514. Each J-shaped hook 512 has a substantially circular cross-sectional shape with a diameter, D, of about 1 cm. The hook may have a length, L, of about 20 cm. The hook may have a width, W, of about 6 cm. The hooks 512 exhibit a smooth curvature to form the two arms that are substantially parallel to one another. The hooks 512 are formed from a material that will have relatively low sliding friction with the material of the sample pant, such as TEFLON-coated steel. Each hook 512 has an attachment member 514 that may be used to attach the hook to the tensile tester. Appropriate dimensions of the attachment member 514 may be varied to meet the needs of the tensile tester used. An engaging arm 516, the portion of the hook 512 that engages the sample pant, may be pivotally attached to the rest of the hook 512 such that the engaging arm 516 may rotate about its axis, which is the center of its cross-sectional face. The distance between the J-shaped hooks 512 is the gauge length, G. The sample pant is measured to the nearest millimeter along the sample pant's waist edge to determine the circumference of the waist opening of the article.

Figure 6B:
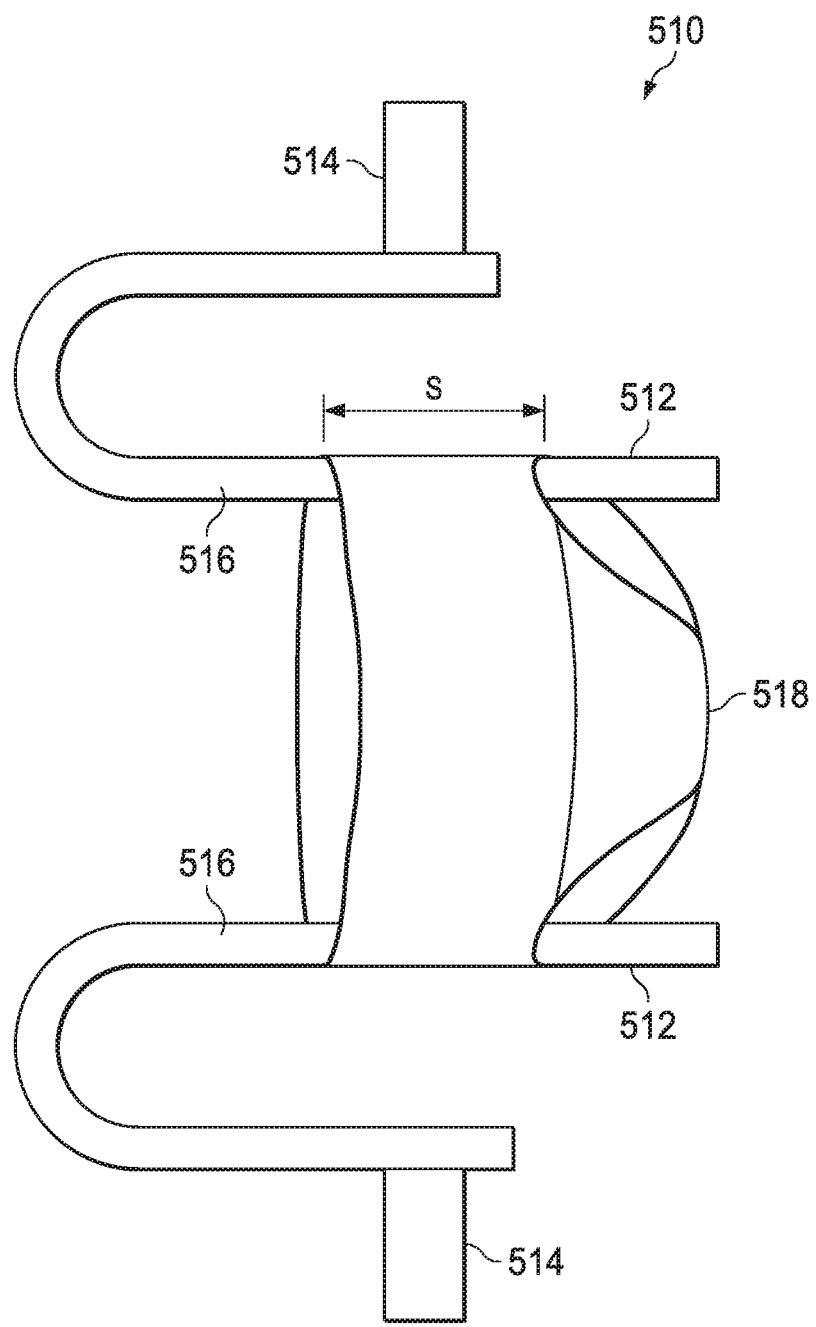

For the measurement, the sample pant 518 is loaded onto the hooks 512 as depicted in FIG. 6B. The sample pant hip length, S, is the width of the portion of the sample pant that is in contact with the J-shaped hooks measured. The sample pant 518 is positioned so that the sample pant's waist edge is positioned substantially perpendicularly with the engaging arms 516 of the J-shaped hooks 512. The J-shaped hooks 512 are inserted into the waist opening and then out the respective leg openings. The respective sides of the sample pant (e.g., at side seams, if present) should be adjacent to the respective engaging arms 516. The sample pant is slid onto the J-shaped hooks until the middle point of the sample pant hip length S is aligned with the center of the attachment member 514.

The sample pant 518 to be measured by this method should not be cut or modified prior to the test. If the sample pant 518 comprises a fastening mechanism around the waist circumference and the fastener(s) are engaged when the sample pant 518 is pulled out of a commercial package, do not disengage, re-engage the fastener(s) or adjust the waist circumference prior to the test.

The measurement method is as follows:
1. Attach both upper and lower J-shaped hooks to the tensile tester.
2. Calibrate the tester according to the manufacture's manual.
3. Set initial gauge length. The initial gauge length is large enough so that a sample pant 518 can be slid onto the upper J-shaped hook without touching the lower J-shaped hook. The gauge length for baby care products is typically greater than 200 mm.
4. Place a sample pant only on the upper J-shaped hook. At this step the sample pant should not be touching the lower J-shaped hook or any other part of the tensile tester.
5. Reset the load to zero.
6. Lower the upper J-shaped hook closer to the lower hook until the sample pant can be placed onto the both upper and lower J-shaped hooks, as shown in the FIG. 6B. Adjust the gauge length so that the reading of the force is 0N+/−0.05N.
7. Extend the gauge length and stop when the force reaches 0.2N. The head speed should be between 100 and 254 mm/min. The stress relaxation of the elastomer(s) in the sample pant may decrease the force reading but the gauge length should not be adjusted till the gauge length measurement is completed.
8. Measure the gauge length G. The Relaxed Lateral Size=2 G+5.14 D.
9. Extend the gauge length and stop when the force reaches 20N. The head speed should be between about 254 mm/min. The stress relaxation of the elastomer(s) in the sample pant may decrease the force reading but the gauge length should not be adjusted till the gauge length measurement is completed.
10. Measure the gauge length G. The Stretched Lateral Size=2 G+5.14 D.

In view of the foregoing description, the following non limiting examples of pants are contemplated:
1. A disposable absorbent pant adapted to snugly fit an infant or child weighing 75 pounds (34 kg) or less without tearing or separating at seams or other unions of components, having a front waist region, a rear waist region, a crotch region, a waist opening and a pair of leg openings, comprising:
   an absorbent chassis comprising a liquid permeable topsheet, a liquid impermeable backsheet and an absorbent core disposed therebetween, the chassis having forward and rearward ends each attached to a belt;
   the belt comprising front and rear belt portions defining front and rear waist edges that form a waist opening edge, and left and right leg opening edges; the belt having a relaxed lateral size and a stretched lateral size that is at least 150% of the relaxed lateral size; the relaxed lateral size being no more than 400 mm, and left and right side seams at which the front and rear belt portions are joined;
   each of the front and rear belt portions comprising a laminate of:
   a laterally pre-strained elastic film member disposed between a first nonwoven layer and a second nonwoven layer, wherein gathers are present in the first and second nonwoven layers when the belt portions are in a relaxed condition;
   the front belt portion further comprising a front waistband elastic member overlying or underlying the elastic film member, disposed and laterally extending along the front waist edge; and
   the rear belt portion further comprising a rear waistband elastic member overlying or underlying the elastic film member, disposed and laterally extending along the rear waist edge.
2. The pant of example 1 wherein the front belt portion further comprises left and right front leg band elastic members overlying or underlying the elastic film member, disposed and extending along left and right front leg opening edges, respectively.
3. The pant of example 2 wherein the rear belt portion further comprises left and right rear leg band elastic members overlying or underlying the elastic film member, disposed and extending along left and right rear leg opening edges, respectively.
4. The pant of either of examples 2 or 3 wherein one or both of the front leg band elastic members and the rear leg band elastic members follow a curved path.
5. The pant of any of examples 2-4 wherein at least one of the front and rear leg band elastic members is one or more strands of elastomeric material.
6. The pant of any of the preceding examples wherein the laterally pre-strained elastic film member extends at least 90% of the width of the front belt portion between the left and right side seams.
7. The pant of any of the preceding examples further comprising a rear lateral supplemental elastic member distinct from the elastic film member, extending laterally across at least a portion of the rear belt portion, disposed longitudinally between the rear waistband elastic member and the rear leg band elastic members.
8. The pant of example 6 further comprising a front lateral supplemental elastic member distinct from the elastic film member, extending laterally across at least a portion of the front belt portion, and disposed longitudinally between the front waistband elastic member and the front leg band elastic members; and longitudinally offset from the rear lateral supplemental elastic member.
9. The pant of example 8, wherein the rear lateral supplemental elastic member is disposed longitudinally closer to the waist edge than the front lateral supplemental elastic member.

10. The pant of any of the preceding examples, wherein at least one of the front and rear waistband elastic members is one or more strips of elastomeric material.
11. The pant of any of examples 1-9, wherein at least one of the front and rear waistband elastic members is one or more strands of elastomeric material.
12. The pant of any of the preceding examples wherein at least one of the front and rear leg band elastic members is one or more strips of elastomeric material.
13. The pant of any of the preceding examples wherein at least one of the front and rear lateral supplemental elastic members is one or more strips of elastomeric material.
14. The pant of example 10 wherein the one or more strips of elastomeric material is formed by folding over a portion of the laterally pre-strained elastic film member
15. The pant of any of examples 1-12 wherein at least one of the front and rear lateral supplemental elastic members is one or more strands of elastomeric material.
16. The pant of any of the preceding examples wherein the laterally pre-strained elastic film member is apertured.
17. The pant of any of the preceding examples wherein the absorbent core comprises at least 75%, more preferably at least 85%, still more preferably at least 95% by weight absorbent gelling material.
18. The pant of any of the preceding examples wherein the absorbent core comprises a plurality of substantially longitudinally-oriented channels through absorbent material comprised by the absorbent core.
19. The pant of any of the preceding examples wherein at least one of the first nonwoven layer and the second nonwoven layer is a single, continuous section of material extending from the front belt portion to the rear belt portion and forms a layer of each.
20. The pant of example 19 wherein the at least one of the first nonwoven layer and the second nonwoven layer is cut along each leg opening in a concave profile.
21. The pant of any of the preceding examples wherein at least one of the first nonwoven and the second nonwoven has been pre-bonded in a pattern thermal bonds prior to lamination with the elastic film member.
22. The pant of any of the preceding examples wherein the first nonwoven layer and the second nonwoven layer differ by one of more of basis weight, fiber composition, fiber structure, nonwoven structure, fiber hydrophobicity/hydrophilicity, opacity, color, and presence or configuration of printing.
23. The pant of any of the preceding examples wherein the layers of the laminate are bonded together by a pattern of adhesive.
24. The pant of any of the preceding examples wherein the layers of the laminate are bonded together by a pattern of thermal bonds.
25. The pant of any of the preceding examples in which a portion of the elastic film member of one or both the front and rear belt portions does not extend across the chassis.
26. The pant of any of the preceding examples in which the elastic film member of one or both the front and rear belt portions extends across the chassis.
27. The pant of example 26 wherein a portion of the elastic film member is deactivated at at least a portion thereof that lies over the chassis.
28. The pant of any of the preceding examples wherein one or more of the waistband elastic members, leg band members and lateral supplemental elastic members is pre-strained.
29. The pant of any of the preceding examples wherein the rear belt portion has a greater longitudinal height than the front belt portion.
30. The pant of example 29 wherein the rear belt portion has leg cutouts extending from the chassis to the side seams.
31. The pant of any of the preceding examples wherein the relaxed lateral size is no more than 350 mm.
32. The pant of any of the preceding examples wherein the relaxed lateral size is no more than 300 mm.
33. The pant of any of the preceding examples wherein the stretched lateral size is at least 250% of the relaxed lateral size.
34. The pant of any of the preceding examples wherein at least one of the left and right side seams comprises a fastening system by which the front and rear belt portions are non-destructively detachable from and refastenable to each other.
35. The pant of any of the preceding examples wherein the stretched lateral size is no more than 300% of the relaxed lateral size.
36. The pant of any of the preceding examples wherein the stretched lateral size is from 175% to 300% of the relaxed lateral size.
37. The pant of any of the preceding examples wherein the stretched lateral size is from 200% to 300% of the relaxed lateral size.
38. The pant of any of the preceding examples wherein one or both of the first and second nonwoven layers in one or both of the front and rear belt portions has a pattern of apertures therethrough.

All patents and patent applications (including any patents which issue thereon) referred to herein are hereby incorporated by reference to the extent that it is consistent herewith.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is, therefore, intended that the scope of the invention is limited only by the appended claims and equivalents thereof.

What is claimed is:
1. A disposable absorbent pant adapted to snugly fit an infant or child weighing 75 pounds (34 kg) or less without tearing or separating at seams or other unions of components, having a front waist region, a rear waist region, a crotch region, a waist opening and a pair of leg openings, comprising:
 an absorbent chassis comprising a liquid permeable topsheet, a liquid impermeable backsheet and an absorbent core disposed therebetween, the chassis having forward and rearward ends each attached to a belt;

the belt comprising front and rear belt portions defining front and rear waist edges that form a waist opening edge, and left and right leg opening edges; the belt having a relaxed lateral size and a stretched lateral size that is at least 150% of the relaxed lateral size; the relaxed lateral size being no more than 400 mm, and left and right side seams at which the front and rear belt portions are joined;

each of the front and rear belt portions comprising a laminate of:

a laterally pre-strained elastic film member disposed between a first nonwoven layer and a second nonwoven layer, wherein gathers are present in the first and second nonwoven layers when the belt portions are in a relaxed condition;

the front belt portion further comprising a front waistband elastic member overlying or underlying the laterally pre-strained elastic film member, disposed and laterally extending along the front waist edge;

the rear belt portion further comprising a rear waistband elastic member overlying or underlying the laterally pre-strained elastic film member, disposed and laterally extending along the rear waist edge; and a rear lateral supplemental elastic member distinct from the laterally pre-strained elastic film member and from the rear waistband elastic member, extending laterally across at least a portion of the rear belt portion, disposed longitudinally between the rear waistband elastic member and left and right rear leg opening edges and longitudinally closer to the rear waistband elastic member than to the left and right rear leg opening edges; wherein the rear lateral supplemental elastic member is disposed longitudinally closer to the waist edge than a front lateral supplemental elastic member.

2. The pant of claim 1 wherein the front belt portion further comprises left and right front leg band elastic members overlying or underlying the elastic film member, disposed and extending along left and right front leg opening edges, respectively.

3. The pant of claim 2 wherein the rear belt portion further comprises left and right rear leg band elastic members overlying or underlying the elastic film member, disposed and extending along the left and right rear leg opening edges, respectively.

4. The pant of claim 1 wherein the laterally pre-strained elastic film member extends at least 90% of the width of the front belt portion between the left and right side seams.

5. The pant of claim 1 further comprising the front lateral supplemental elastic member distinct from the elastic film member and from the front waistband elastic member, extending laterally across at least a portion of the front belt portion, and disposed longitudinally between the front waistband elastic member and left and right front leg opening edges, and being longitudinally offset from the rear lateral supplemental elastic member.

6. The pant of claim 1 wherein the laterally pre-strained elastic film member is apertured.

7. The pant of claim 1 wherein at least one of the first nonwoven layer and the second nonwoven layer is a single, continuous section of material extending from the front belt portion to the rear belt portion and forms a layer of each.

8. The pant of claim 1 wherein at least one of the first nonwoven and the second nonwoven has been pre-bonded in a pattern thermal bonds prior to lamination with the elastic film member.

9. The pant of claim 1 wherein a portion of the laterally pre-strained elastic film member of at least one of the front and rear belt portions is deactivated at at least a portion thereof that lies over the chassis.

10. The pant of claim 1 wherein the rear belt portion has a greater longitudinal height than the front belt portion.

11. The pant of claim 1 wherein the relaxed lateral size is no more than 350 mm.

12. The pant of claim 1 wherein the stretched lateral size is from 175% to 300% of the relaxed lateral size.

13. The pant of claim 1 having side seams joining the front and rear belt portions, wherein the side seams are refastenable.

* * * * *